United States Patent [19]

Neef et al.

[11] Patent Number: 4,603,013

[45] Date of Patent: Jul. 29, 1986

[54] ESTRANE DERIVATIVES

[75] Inventors: Günter Neef; Karl Petzoldt; Gerhard Sauer; Helmut Hofmeister, all of Berlin, Fed. Rep. of Germany

[73] Assignee: Schering Aktiengesellschaft, Berlin and Bergkamen, Fed. Rep. of Germany

[21] Appl. No.: 644,465

[22] Filed: Aug. 27, 1984

[30] Foreign Application Priority Data

Aug. 26, 1983 [DE] Fed. Rep. of Germany ....... 3331288

[51] Int. Cl.[4] ................................................. C07J 1/00
[52] U.S. Cl. ............................... 260/397.3; 260/397.4; 435/54
[58] Field of Search ..................... 260/397.4

[56] References Cited

U.S. PATENT DOCUMENTS 3,179,674  4/1965  Laskin et al. ...................... 260/397.4
3,243,355  3/1966  Holmlund et al. ................. 260/397.4
3,766,224  10/1973  Coombs ............................ 260/397.4

FOREIGN PATENT DOCUMENTS 1223372  8/1966  Fed. Rep. of Germany ... 260/397.4

OTHER PUBLICATIONS

CA: vol. 96 (5) Par. 35638y, Abstract of Ger. (East) DD 147. 946–Pat. Apr. 29, 1981, Kasch et al.

Primary Examiner—Elbert L. Roberts
Attorney, Agent, or Firm—Millen & White

[57] ABSTRACT

Estrane derivatives of the general formula I

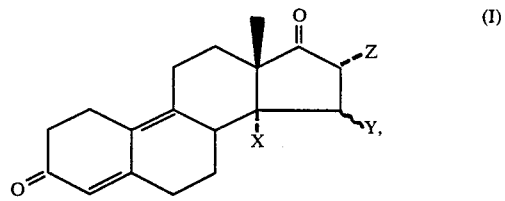

wherein one of the substituents X or Z signifies a hydrogen atom and the other together with Y represents a carbon-carbon bond, or wherein the substituents X and Z represent hydrogen atoms and Y represents an α-position hydroxy group or a β-position alkyl group with up to 6 carbon atoms, are valuable intermediates for preparation of pharmacologically effective substances.

8 Claims, No Drawings

ESTRANE DERIVATIVES

BACKGROUND OF THE INVENTION

This invention relates to new estrane derivatives having valuable uses. It is known that producing 15 β-alkyl steroids chemically causes considerable difficulties.

SUMMARY OF THE INVENTION

Accordingly, it is an object of this invention to provide improved methods of preparing such compounds, compounds for use in such methods, and the products so produced.

Upon further study of the specification and appended claims, further objects and advantages of this invention will become apparent to those skilled in the art.

These objects have been achieved by providing estrane derivatives of formula I

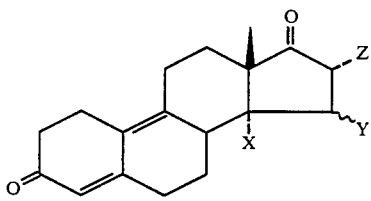

wherein
one of the substituents X or Z is hydrogen and the other together with Y represents a carbon-carbon bond, or wherein the substituents X and Z are both hydrogen atoms and Y is an α-position hydroxy group or a β-position alkyl group of up to 6 carbon atoms.

Such compounds include,
15 α-hydroxy-4,9-estradiene-3,17-dione,
4,9,14-estratriene-3,17-dione,
4,9,15-estratriene-3,17-dione,
15 β-methyl-4,9-estradiene-3,17-dione, and
15 β-n-butyl-4,9-estradiene-3,17-dione.

They have also been achieved by providing a process for the production of estrane derivatives of formula I wherein 4,9-estradiene-3,17-dione is fermented with a fungus culture of *Fusarium oxysporium, Glomerella glycines, Glomerella fusaroides, Abisida coerulea* to obtain the 15 α-OH product,
optionally, the resulting 15 α-hydroxy-4,9-estradiene-3,17-dione is converted to the trimethyl acetate or the phenylsulfenyl ester, and the trimethylacetyl group or the phenylsulfenyl group is split off by means of bases to eventually selectively form the 15-ene or 14-ene compound, respectively, and, optionally, the resulting 4,9,15-estratriene-3,17-dione is β-alkylated with a copper alkyl compound of formula II or III $$R_2CuLi \qquad (II)$$

or $$R_2Cu(CN)Li_2 \qquad (III),$$

wherein
R is an alkyl radical of up to 6 carbon atoms.

DETAILED DESCRIPTION

It has now been found that 4,9-estradiene-3,17-dione can be hydroxylated in the 15 α-position in a surprising way with the strains mentioned above. This first reaction step of the process according to this invention can be performed under the fully conventional conditions that are usually used in microbiological hydroxylations of steroids with fungus cultures. See, e.g., whose disclosure is incorporated by reference herein. In the usual routine preliminary tests, the most favorable fermentation conditions, such as, for example, selection of the most favorable nutrient medium, suitable substrate solvent or suspension agent, substrate concentration, technical conditions such as temperature, aeration, pH and optimal methods for germination, substrate addition and substrate contact with the enzyme of the microorganism, etc., can easily be determined, e.g., using analytical methods, especially by thin-layer chromatography.

It is advantageous to use the substrate in a concentration of about 100 to 200 mg per liter of nutrient medium. The pH is preferably set in the range of 5 to 7. The growing temperature is in the range of 20° to 40° C., preferably from 25° to 35° C. Preferably 0.5 to 5 liters of air per minute per liter of culture broth is supplied for aeration. The conversion of the substrate is advantageously followed by thin-layer chromatographic analysis. The fermentation period is usually about 15 to 40 hours.

The ability of the species disclosed above to carry out the 15α-hydroxylation of this invention extends to all strains of each of these species in view of experimental results. The ability of each strain of each of these species to effect the 15α-hydroxylation is derived from a characteristic of each species which extends to each of the strains.

If the dehydration of the 15 α-hydroxy-4,9-estradiene-3,17-dione, which optionally follows, is performed using the conventional reactants that are usually applied, then mixtures of 4,9,14- and 4,9,15-estratriene-3,17-diones are obtained.

4,9,14-estratriene-3,17-dione can be selectively produced, however, if the 15 α-hydroxy compound is esterified with phenylsulfenyl chloride or an equivalent. Conditions of this reaction are not critical and are routinely selected.

The phenylsulfenyl group is then split off by means of bases, generally at a temperature of −70° to 30° C.

Suitable bases, for example, include triethylamine, N-methylpiperidine or N-methylmorpholine. It is not necessary to isolate the phenylsulfenyl ester; rather, it can be split off in situ directly after it is formed.

If 15 α-hydroxy-4,9-estradiene is reacted with trimethylacetic anhydride (pivalic antydride) or trimethylacetyl chloride or an equivalent in the presence of bases, preferably 4-dimethylaminopyridine, the preferred 4,9,15-estratriene-3,17-dione is selectively obtained. Conditions of this reaction are not critical and are routinely selected.

Here too, it is not necessary to isolate the intermediately formed trimethylacetyl compound.

Alkylation of the 4,9,15-estratriene-3,17-dione, to selectively form the 15 β-alkylderivative, which optionally follows, is performed under the conditions that are well known to a man skilled in the art. See, e.g., M. Fieser, Reagents for Organic Synthesis, Vol 2, pages 151-153 and J. Am. Chem. Soc., 103, 7672, 1981, whose disclosure is incorporated by reference herein.

The 14-ene compound can be used in the preparation of the corresponding 14-β-H-steroid by conventional hydrogenation. The latter is a known intermediate for the preparation of corresponding pharmacological active steroids.

Thereafter, the 15 β-alkyl compound is prepared as described herein via the 15 α-OH and 15-ene compounds.

The 15 β-alkyl-4,9-estradiene-3,17-diones thus produced are valuable intermediates for production of pharmacologically effective steroid hormones. Thus, for example, according to the process described in Bull. Soc. Chem. France, 1970, 2548 ff and 2556 ff, whose disclosures are incorporated by reference herein, these compounds can be converted into the corresponding compounds of formula IV

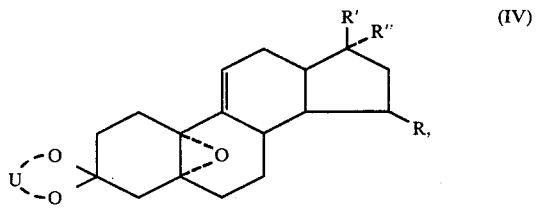

or of formula V

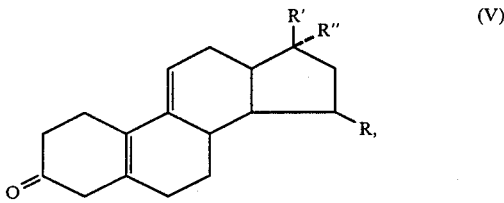

wherein
R is alkyl of 1-6 C-atoms, U is alkylene of 2 to 6 carbon atoms, R' is a free, esterified or silylated hydroxy group, and R" is cyano or an aliphatic hydrocarbon group of 1 to 4 carbon atoms.

Suitable alkyl groups above are methyl, ethyl and straight chained or branched propyl, butyl, pentyl or hexyl. Suitable alkylene groups U can also be straight chained or branched. Ester groups in $R^1$ include conventional esterifying groups, e.g., acyl groups of $C_{1-8}$-hydrocarbon carboxylic acids and silylation groups include tri($C_{1-4}$-alkyl or phen-$C_{1-4}$-alkyl)-silyl groups, e.g., trimethylsilyl, dimethyl-tert-butyl silyl or tribenzylsily. Suitable $R^4$ groups are alkyl, alkenyl or alkynyl groups. See the above-mentioned references for definitions of the compounds of Formula IV and V.

The compounds of the formula V are known intermediates for the preparation of steroids of antigestagenic activity. See, e.g., U.S. Pat. No. 4,386,085.

Analogously to the methods described in German laid-open specification No. 29 20 184, in European patent application No. 57115, in Tetrahedron Letters 22, 1971, 2005, or Tetrahedron Letters 22, 1979, 2051, all of whose disclosures are incorporated by reference herein, the compounds of general formula IV, thus obtained, can also be converted to 15 β-alkylated steroids which have the same spectrum of activity as the corresponding 16-alkylated steroids or the corresponding steroids unsubstituted in the 15-position, e.g., as Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

500 ml of a sterile nutrient solution of the following composition: 3% glucose, 1% corn steep liquor, 0.2% sodium nitrate, 0.1% potassium hydrogen phosphate, potassium dihydrogen phosphate, 0.05% magnesium sulfate, 0.002% iron(II) sulfate, 0.05% potassium chloride are inoculated with a 10-day-old slant agar culture of Fusarium oxysporum (ATCC 7808) and shaken for 2½ days at 30° C. This initial culture is used for inoculation of a 20-liter profermentor which is charged with 15 liters of a sterile medium. The composition of the medium is the same as given above. The pH is 6.0.

The initial culture is further developed in the profermentor for 24 hours with stirring (200 rpm) and aeration (15 l/min) at 29° C.

Every 900 ml of an initial culture thus obtained is transferred to a 20-liter main fermentor, whose content consists of 14.1 liters of sterile medium.

The composition of the media is: 3% glucose, 1% corn steep liquor, 0.2% sodium nitrate, 0.1% potassium hydrogen phosphate, 0.2% potassium dihydrogen phosphate, 0.05% magnesium sulfate, 0.002% iron(II) sulfate, 0.05% potassium chloride. The pH is 6.15.

The culture is further developed in the main fermentor with stirring at 220 rpm and aeration of 15 liters of air per minute at 29° C. Addition of the substrate occurs after 12 hours.

7.5 g of 4,9(10)-estradiene-3,7-dione are dissolved in 100 ml of N,N-dimethylformamide, sterilized by filtration and added to the culture. The substrate concentration amounts to 500 mg/l. Aeration is set at 5 liters of air/minute and fermentation is continued.

Control of the reaction is performed by thin-layer chromatography on precoated silica gel plates 60 F 254 Merck.

After complete conversion of the initial product (24 hours contact time), the fermentor ingredients are filtered off from the mycelium. The filtrate and mycelium are extracted with methyl isobutyl ketone. The extracts are combined and concentrated in vacuo at 30° to 35° C. The residue is washed with hexane to remove the antifoaming agent, Silikon SH. The crude product is chromatographed with a silica gel column with methylene chloride/ethanol. The corresponding fractions are combined and recrystallized from ethyl acetate.

With a total charge of 66 g of initial product, 19.5 g of 15α-hydroxy-4,9(10)-estradiene-3,17-dione with a melting point of 156° to 157° C. are obtained. Yield: 27.9% of theory.

As a further reaction product, the dihydroxylated compound 11β,15α-dihydroxy-4,9(10)-estradiene-3,17-dione was found. 8.4 g=11.3% of theory with a melting point of 147°/149° to 151° C.

EXAMPLE 2

30.82 g of 4,9(10)-estradiene-3,17-dione in a substrate concentration of 250 mg/l are fermented under the conditions of example 1. The contact time amounts to 22 hours. The yield in 15α-hydroxy-4,9(10)-estradiene-3,17-dione amounts of 10 g=30.6% of theory with a melting point of 157°/158° to 161° C.

Of dihydroxylated compound, 4.6 g=13.3% of theory of 11β,15α-dihydroxy-4,9-(10)-estradiene-3,17- dione with a melting point of 146°/147° to 149° C. are produced.

EXAMPLE 3

30 g of 4,9(10)-estradiene-3,17-dione in a substrate concentration of 400 mg/l are fermented under the conditions of example 1. The contact time amounts to 22 hours. The yield in 15α-hydroxy-4,9(10)-estradiene-3,17-dione amounts to 10.3 g=32.3% of theory with a melting point of 158°/159° to 160° C.

Of dihydroxylated compound, 4.3 g=12.8% of theory of 11β,15α-dihydroxy-4,9,(10)-estradiene-3,17-dione with a melting point of 146°/147° to 149° C. are produced.

EXAMPLE 4

27 g of 4,7,9(10)-estradiene-3,17-dione are fermented in a substrate concentration of 650 mg/l under the conditions of example 1. The contact time amounts to 24½ hours. The yield of 15α-hydroxy-4,9(10)-estradiene-3,17-dione amounts to 9 g=31.4% of theory with a melting point of 158°/159° to 160° C.

Of dihydroxylated compound, 3.4 g=11.2% of theory of 11β,15α-dihydroxy-4,9(10)-estradiene-3,17-dione with a melting point of 146°/147° to 149° C. are produced.

EXAMPLE 5

7.05 g of 4,9(10)-estradiene-3,17-dione are fermented with the strain Glomerella fusaroides ATCC 9552 in a substrate concentration of 250 mg/l under the conditions of example 1. The contact time amounts to 17½ hours.

The yield in 15α-hydroxy-4,9(10)-estradiene-3,17-dione amounts to 1.59 g=21.2% of theory with a melting point of 146°/148° to 150° C.

11β,15α-dihydroxy-4,9(10)-estradiene-3,17-dione 0.07 g=0.9% of theory with a melting point of 140°/141° to 142° C.

EXAMPLE 6

4,9,15-estratriene-3,17-dione

A suspension of 19.5 g of 15α-hydroxy-4,9-estradiene-3,17-dione in 300 ml of toluene is mixed, under ice water cooling, successively with 26.5 g of pivalic acid anhydride and 18.6 g of 4-dimethylaminopyridine. Stirring is then performed for 72 hours at room temperature, then the reaction solution is poured into saturated sodium hydrogen carbonate solution, stirred for 30 more minutes at room temperature and extracted with ethyl acetate. The ethyl acetate extracts are washed with saturated ammonium chloride solution and saturated sodium chloride solution, dried with sodium sulfate and concentrated in a water jet vacuum. The crude product, thus obtained, is filtered with aluminum oxide, Merck, neutral, step III, with hexane/ethyl acetate. The main fraction is crystallized from ethyl acetate. 14.4 g (79% of theory) of 4,9,15-estratriene-3,17-dione with a melting point of 182° to 183° C. are obtained.

EXAMPLE 7

15β-methyl-4,9-estradiene-3,17-dione 5.2 ml of a 5% solution of methyllithium in diethyl ether are mixed with 570 mg of copper(I) iodide by portions at −5° C. Stirring is performed at a temperature between −5° and 0° C. until the copper iodide is fully dissolved. Then it is cooled to −20° C. and a solution of 1.1 g of 4,9,15-estratriene-3,17-dione in 15 ml of absolute tetrahydrofuran is slowly added drop by drop. It is stirred for 20 minutes at −20° C., then poured in concentrated aqueous ammonia solution and extracted with ethyl acetate. After chromatography with silica gel with hexane/ethyl acetate and crystallization of the main fraction from ethyl acetate/diisopropyl ether, 720 mg of 15β-methyl-4,9-estradiene-3,17-dione with a melting point of 125° to 126° C. are obtained.

EXAMPLE 8

15β-n-Butyl-4,9-estradiene-3,17-dione 6.25 ml of a 15% solution of n-butyllithium in hexane are added to a suspension of 500 mg of copper(I) cyanide in 10 ml of absolute tetrahydrofuran drop by drop at −78° C. After addition, it is stirred for 15 minutes more at −78° C., before a solution of 1.2 g of 4,9,15-estratriene-3,17-dione in 20 ml of absolute tetrahydrofuran is added drop by drop. Then it is stirred for 90 minutes, during which the temperature of the reaction solution is allowed gradually to rise to −20° C. For finishing, it is poured in concentrated aqueous ammonia solution and extracted with ethyl acetate. After recrystallization of the crude product from ethyl acetate/diisopropyl ether, 940 mg of 15β-n-butyl-4,9-estradiene-3,17-dione with a melting point of 159° to 161° C. are obtained.

EXAMPLE 9

4,9,14-estratriene-3,17-dione

A solution of 1.5 g of 15 α-hydroxy-4,9-estradiene-3,17-dione in 20 ml of methylene chloride and 1.2 ml of triethylamine is mixed with a solution of 0.83 g of phenylsulfenyl chloride in 5 ml of methylene chloride drop by drop at −20° C. After addition, stirring is performed for 10 minutes at −20° C., the reaction solution is then diluted with 100 ml of methylene chloride, washed, one after the other, with saturated sodium hydrogen carbonate solution and saturated ammonium chloride solution, dried with sodium sulfate and concentrated. Crystallization of the crude product from ethyl acetate/diisopropyl ether yields 1.24 g (88.2% of theory) of 4,9,14-estratriene-3,17-dione with a melting point of 143° to 144° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An estrane derivative of the formula

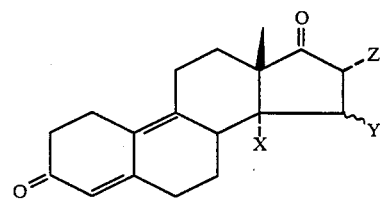

wherein one or X or Z is hydrogen and the other together with Y is a carbon-carbon bond, or wherein X and Z both are hydrogen atoms and Y is α-hydroxy.

2. 15α-Hydroxy-4,9-etradiene-3,17-dione, a compound of claim 1.

3. 4,9,14-Estratriene-3,17-dione, a compound of claim 1.

4. 4,9,15-Estratriene-3,17-dione, a compound of claim 1.

5. A process for the preparation of 15 α-hydroxy-4,9-estradiene-3,17-dione comprising fermenting 4,9-estradiene-3,17-dione with a fungus culture of *Fusarium oxysporum,* or *Absida coerulea.*

6. A process for preparing 4,9,14-estratriene-3,17dione comprising reacting trimethyl acetic anhydride or trimethyl acetyl chloride with 15α-hydroxy-4,9-estradiene-3,17-dione to form the corresponding 15 α-ester, and splitting off the 15 α-ester group with a base there by eventually selectively forming the corresponding 14-ene compound.

7. A process for preparing 4,9,15-estratriene-3,17dione comprising reacting phenylsulfenyl chlorids with 15 α-hydroxy-4,9-estradiene-3,17-dione to form the corresponding 15 α-ester, and splitting off the 15 α-ester groups with a base thereby eventually selectively forming the corresponding 15-ene compound.

8. A process for preparing a 15 β-$C_{1-6}$-alkyl-4,9-estradiene-3,17-dione, comprising alkylating 4,9,15-estratriene-3,17-dione by reacting it with a copper alkyl compound of formula II or III $$R_2CuLi \qquad (II)$$

or $$R_2Cu(CN)Li_2 \text{ tm (III),}$$

wherein
R is an alkyl group of up to 6 carbon atoms.

* * * * *